(12) United States Patent
Burmeister

(10) Patent No.: US 11,090,402 B2
(45) Date of Patent: Aug. 17, 2021

(54) FLEXIBLE DIVIDER FOR FILTER BASKETS

(71) Applicant: AESCULAP AG, Tuttlingen (DE)

(72) Inventor: Christoph Burmeister, Singen (DE)

(73) Assignee: AESCULAP AG, Tuttlingen (DE)

( * ) Notice: Subject to any disclaimer, the term of this patent is extended or adjusted under 35 U.S.C. 154(b) by 49 days.

(21) Appl. No.: 16/496,607

(22) PCT Filed: Feb. 23, 2018

(86) PCT No.: PCT/EP2018/054463
§ 371 (c)(1),
(2) Date: Sep. 23, 2019

(87) PCT Pub. No.: WO2018/192703
PCT Pub. Date: Oct. 25, 2018

(65) Prior Publication Data
US 2020/0384143 A1 Dec. 10, 2020

(30) Foreign Application Priority Data
Apr. 21, 2017 (DE) .......................... 102017206780.2

(51) Int. Cl.
*A61L 2/26* (2006.01)
*B65D 25/06* (2006.01)

(52) U.S. Cl.
CPC ................ *A61L 2/26* (2013.01); *B65D 25/06* (2013.01); *A61L 2202/24* (2013.01)

(58) Field of Classification Search
None
See application file for complete search history.

(56) References Cited

U.S. PATENT DOCUMENTS

2008/0314789 A1 12/2008 Thomas
2010/0176016 A1 7/2010 Pell

FOREIGN PATENT DOCUMENTS

| CN | 201144017 | | 11/2008 | |
|---|---|---|---|---|
| CN | 205514939 U | | 8/2016 | |
| DE | 9411155 U1 | | 9/1994 | |
| DE | 102004008455 B3 | | 8/2005 | |
| EP | 0705573 A2 | * | 4/1996 | ............. A61B 50/22 |
| EP | 0705573 A2 | | 4/1996 | |

OTHER PUBLICATIONS

EP0705573A2—translated document (Year: 1995).*
International Search Report and Written Opinion for International Application No. PCT/EP2018/054463, dated Jun. 1, 2018—11 pages.

* cited by examiner

*Primary Examiner* — Jelitza M Perez

(57) ABSTRACT

A divider for a sterilization filter basket for sterilizing medical instruments has two lateral wall sections and a central wall section therebetween. The divider is substantially flat in configuration, and the central wall section is perforated by a multiplicity of openings. One lateral wall section or both lateral wall sections has/have a slit-shaped notch, so that the lateral region of the lateral wall section, which is separated by the slit-shaped notch, is formed as a resilient section that has a number of lateral protrusions. If only one lateral wall section is formed in this way, then the other lateral wall section has a number of protrusions that extend at least partially in the lateral direction and at least partially in a direction perpendicular to the extension plane of the central wall section.

20 Claims, 12 Drawing Sheets

FLEXIBLE DIVIDER FOR FILTER BASKETS

CROSS REFERENCE TO RELATED APPLICATIONS

This application is the United States national phase entry of International Application No. PCT/EP2018/054463, filed Feb. 23, 2018, which claims the benefit of priority of German Application No. 10 2017 206 780.2, filed Apr. 21, 2017. The contents of International Application No. PCT/EP2018/054463 and German Application No. 10 2017 206 780.2 are incorporated by reference herein in their entireties.

FIELD

The present invention relates to a divider for a sterilization filter basket and in particular to a divider of this type that can be positioned and installed in a sterilization filter basket without the use of tools.

BACKGROUND

Numerous forms of sterilization filter baskets or filter baskets are known in the prior art. These are used for storing medical instruments and/or implants, for cleaning (i.e. washing) said instruments and implants at least partially in the filter baskets, and for then placing the filter basket along with the instruments and implants in a sterilization container or sterile container. In said sterile container, the filter basket with the instruments and implants contained therein is then sterilized and stored until said instruments and implants are needed during surgery. During preparation for surgery, the filter baskets are removed from the sterile containers and set out for the surgeon. Some of the instruments and implants are left in the filter baskets during preparation, but some are prepared by being removed from the filter baskets and placed on a surgical drape, for example.

To enable instruments and implants to be cleaned reliably in a filter basket, the side walls, the bottom, and—if present—the dividers and optionally the storage racks are equipped with openings, so that the passage of cleaning fluid is impeded as little as possible. Formerly, filter baskets were also made of metal wire mesh. However, since this has the disadvantage that soil can easily accumulate and become lodged at the intersections of the metal wires, most of the medical field has transitioned to producing filter baskets from metal sheets, which are perforated with a multitude of openings.

Filter baskets are available in a very wide variety of sizes and shapes. In some cases, filter baskets are stowed inside other filter baskets. The parts that are placed and stored in the filter baskets may be large, but may also be very small. To prevent these parts from becoming mixed up during cleaning, some filter baskets are equipped with dividers. Partitioning the filter basket into a plurality of areas also facilitates the identification of parts, the removal of these parts from the filter basket, and the safe storage of these parts. Identification is facilitated, for example, by storing pedicle screws of different but similar lengths separately from one another.

In these filter baskets with dividers, the dividers are always fixedly connected to the filter basket, usually by welding or riveting. However, this does not allow a user to adjust the size and shape of the various areas or compartments of his filter basket individually to his own needs. This means either that a manufacturer must produce and supply a very large number of different filter baskets with different layouts or that this demand of the user cannot be met. But producing many different filter baskets in only relatively small piece numbers and keeping these filter baskets on hand is disproportionately costly.

SUMMARY

The object of the present invention is therefore to provide a divider for a sterilization filter basket that will enable the user to partition his sterilization filter basket according to his needs, and thus to produce compartments of individually desired sizes in the sterilization filter basket. A further object of the present invention is to enable the user to accomplish this without the use of tools, and to allow the user to adjust the partitioning to his current needs at any time.

The object of the present invention is attained with a divider for a sterilization filter basket as described herein.

According to a first embodiment of the present invention, a divider for a sterilization filter basket for sterilizing medical instruments is provided, which has two lateral wall sections and a central wall section therebetween. The divider is substantially flat in configuration, although it is also possible for the divider to be fluted or in a zig-zag configuration. Flat in this context refers merely to the fact that the divider forms a dividing wall that is characterized in that it has a significantly greater extension in two spatial directions than in the third spatial direction. The central wall section is configured has having a multiplicity of openings, i.e., it is configured as having perforations across its surface. In addition, one of the two lateral wall sections is equipped with a slit-shaped notch. The lateral region of said lateral wall section is thereby formed as a resilient section. This means that this resilient region, which represents said one lateral edge of the divider, can be deformed elastically toward the central region, thereby decreasing the maximum lateral extension of the divider.

The resilient section is also equipped with a number of protrusions, which extend at least in the lateral direction. Extending at least in the lateral direction means that these protrusions may also extend partially or entirely in a transverse direction, i.e., obliquely, for example, although the extension in the lateral direction is relevant here in order for these protrusions to engage in openings that are provided in a filter basket into which the divider is to be inserted and installed. These protrusions may also extend entirely within the plane that is defined by the dividing wall of the divider. In addition, the slit is wide enough to allow sufficient elastic deformation of the resilient region for the protrusions provided on this resilient region to be disengaged from the perforations of the wall section into which they are inserted to install the divider.

The other lateral wall section likewise has a number of protrusions that extend at least partially in the lateral direction. These protrusions are also intended to engage in openings that are provided in a filter basket.

These latter protrusions are preferably also configured as extending at least partially in a direction that is arranged perpendicular to the plane of extension of the central wall section. This plane of extension is, so to speak, the intermediate wall surface or dividing wall surface that is formed in the filter basket by the divider.

According to an advantageous embodiment of the first aspect of the present invention, the protrusions on the other lateral wall region are substantially L-shaped in configuration. They extend from the other lateral wall section first in the lateral direction and then in a direction running perpendicular to the surface of the central wall section.

According to a second embodiment of the present invention, a divider for a sterilization filter basket for sterilizing medical instruments is provided, which has two lateral wall sections and a central wall section therebetween. The divider is substantially flat in configuration, although it is possible in this case as well for the divider to be fluted or in a zig-zag configuration. Here again, the central wall section is configured as having a multiplicity of openings. Each of the two lateral wall sections has a slit-shaped notch, so that the lateral region of each lateral wall section, which is separated by the slit-shaped notch, is formed as a resilient section. In this embodiment, therefore, a resilient section is provided on each of the two lateral sides of the divider, as described above in reference to the first embodiment. Each of the two resilient sections has a number of protrusions extending at least in the lateral direction.

According to one advantageous embodiment of the second aspect of the present invention, the divider is configured as mirror-symmetrical. This facilitates proper insertion of the divider into a filter basket because it is not necessary to ensure the proper right/left orientation. This means that it makes no difference which side of the divider is inserted first into a filter basket and anchored via the protrusions in the one wall, followed by anchoring of the other side of the divider via the protrusions thereof in the opposite wall.

According to another advantageous embodiment of the second aspect, the divider is configured as rotationally symmetrical. This facilitates proper insertion of the divider into a filter basket because it is not necessary to ensure the proper top/bottom orientation. In this embodiment, the divider no longer has a top and a bottom; instead, a number of protrusions are located on one side in the upper region of the divider, and other protrusions are located on the other side in the lower region of the divider. Thus, regardless of how the divider is oriented, it can be inserted into a filter basket, for example, by first being anchored in one wall of a filter basket via the protrusions in the lower region and then being anchored in an opposite wall via the protrusions on the other side, which accordingly are located in the upper region. Of course, this can also be performed in the reverse order, although the resilient section is easier to deform elastically if it can be grasped in the upper region of the divider and if the protrusions are also in the upper region of the divider. The procedure described above is presumably the easier way to install a corresponding divider according to the invention in a filter basket.

According to one advantageous embodiment of both aspects of the present invention, each lateral wall region has at least two protrusions. This ensures in a simple manner that a divider installed in a filter basket can no longer tilt as a result of transverse forces, since the two protrusions counteract any tilting torque. For this purpose, it is advantageous for the two protrusions on each side to be positioned a certain distance apart from one another.

According to another advantageous embodiment of both aspects of the present invention, on one resilient section a manipulation section is formed. This manipulation section facilitates the elastic deformation of the resilient sections for the purpose of temporarily decreasing the lateral extension of the divider, so that the protrusions provided on the resilient section can first be guided past holes in a filter basket, allowing said protrusions and the entire divider to be positioned, after which said protrusions can be inserted into the desired holes in the filter basket by relaxing the resilient section.

At the same time, a manipulation section of this type provides an intuitive usage instruction to the user, namely that he should grasp the divider at this location and deform it elastically.

The manipulation section is preferably formed between two protrusions. This also ensures at the same time that these two protrusions are at a sufficient distance from one another to absorb tilting torque. Additionally, this ensures in a simple manner that the user will intuitively displace the protrusions elastically toward the center of the divider sufficiently to avoid accidentally getting the protrusions stuck in holes in the filter basket in which the user does not wish the divider to be anchored.

Further preferably, the manipulation section is configured as a lateral recess, for example as an arc-shaped recess. A very simple manipulation section can thereby be formed, which at the same time intuitively indicates to the user that he should deform the resilient section in the direction in which the lateral recess is pointing.

The divider is particularly advantageously made of metal, in particular sheet metal. Metal is extremely well-suited for sterilization equipment, as long as it is a rust-proof metal such as a stainless steel or aluminum or an alloy thereof. If the divider is produced from sheet metal, all structures can be molded from the sheet in a single working step, e.g., by means of stamping, laser cutting, water jet cutting, wire EDM, or the like. For a divider according to the first aspect of the invention, it is then necessary only for a number of protrusions to be optionally molded in the L-shape. For other aspects, this process step is not even necessary. This enables a very simple and fully automatic manufacturing process.

BRIEF DESCRIPTION OF THE DRAWING FIGURES

Further advantages and features of the invention will be apparent to those skilled in the art from the attached figures and from the detailed description of the exemplary embodiments. In the drawings, FIG. 1 shows a view of a divider according to a first exemplary embodiment of the present invention;

DETAILED DESCRIPTION

The first exemplary embodiment of the present invention will be described in detail with reference to FIGS. 1 to 5.

Figure 1:
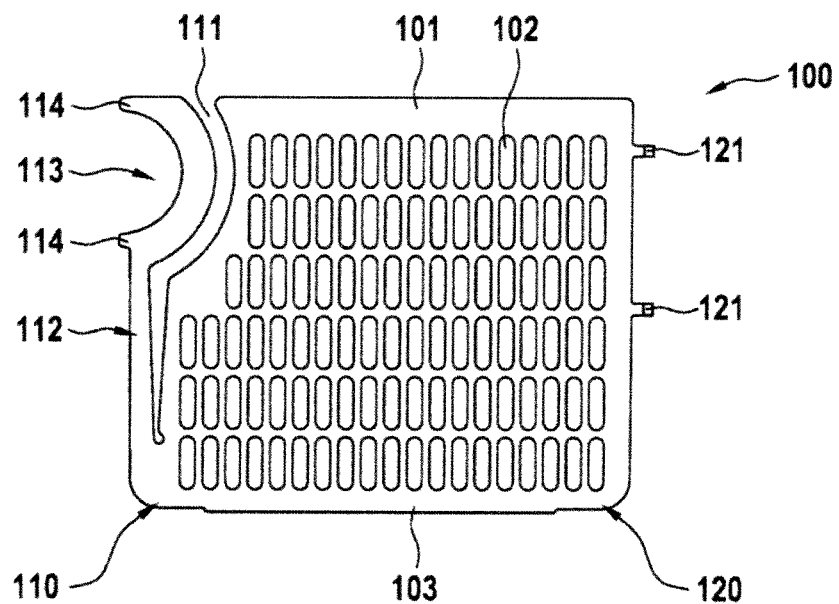
Figure 2:
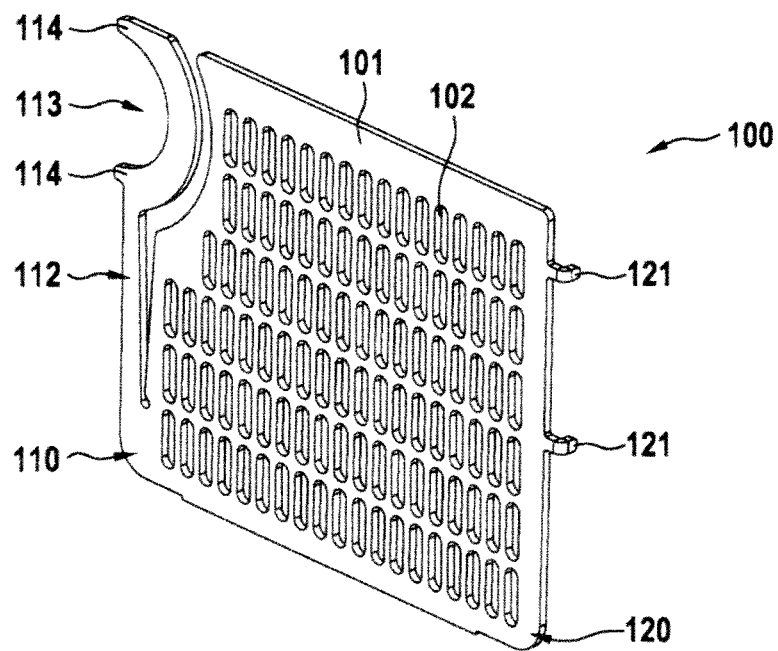
FIG. 2 shows a perspective view of the divider of FIG. 1.
Figure 3A:
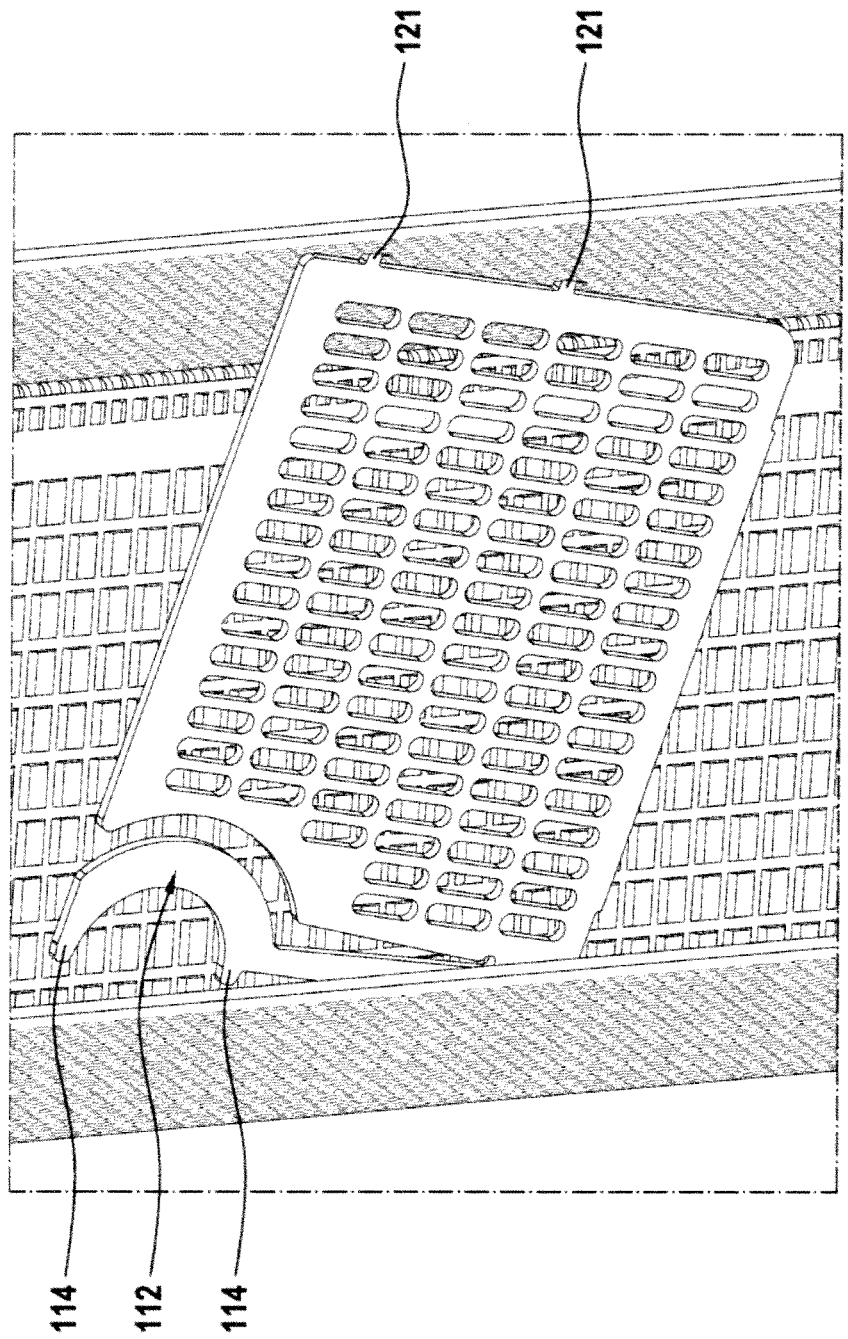
FIGS. 3A and 3B show the start of an installation of a divider of FIG. 1 into a filter basket.
Figure 3B:
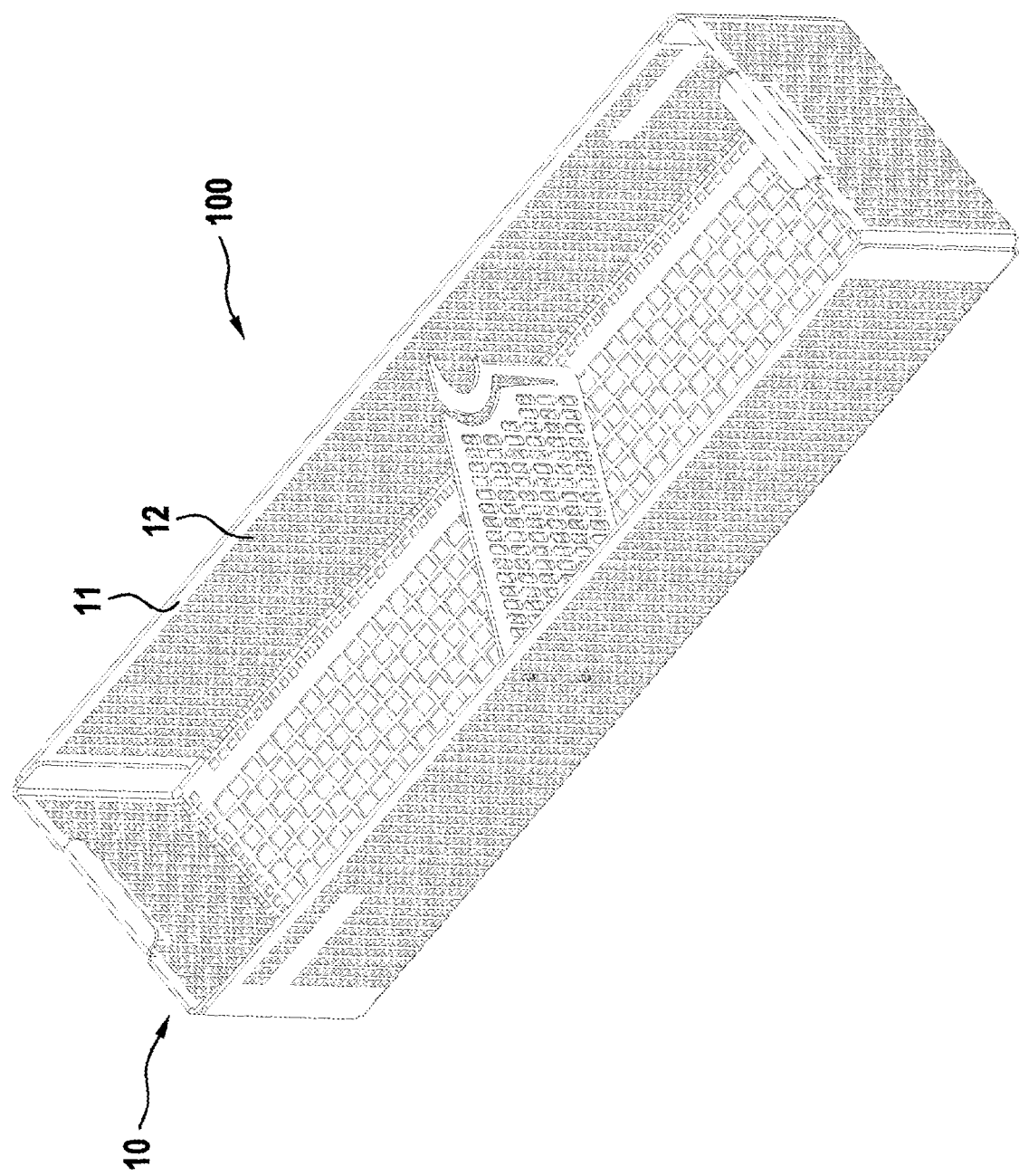
Figure 4A:
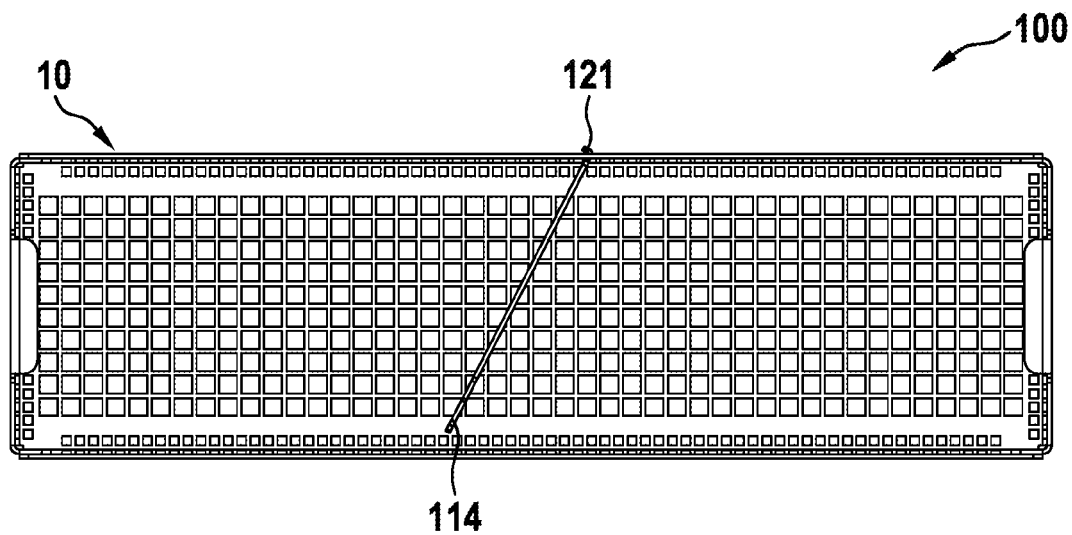
FIGS. 4A and 4B show the progression of an installation of a divider of FIG. 1 into a filter basket.
Figure 4B:
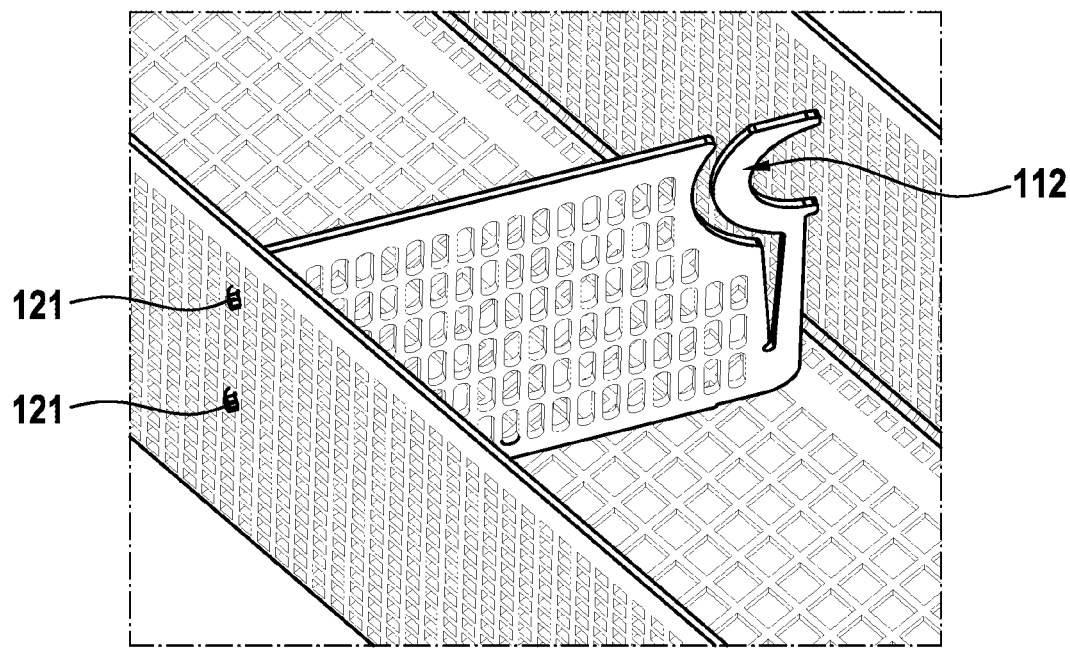

FIG. 1 shows a view of a divider 100 according to the first exemplary embodiment. The divider 100 is produced from a 2-mm-thick stainless steel sheet and has a central wall section 101, a first lateral wall section 110, and a second lateral wall section 120. In the first lateral wall section 110, a slit-shaped notch 111 is formed, which separates a resilient section 112 from the central wall section and gives the resilient section 112 space to be deformed toward the central wall section 101. On the resilient section 112, two lateral protrusions 114 are formed, between which a manipulation section 113 is formed. The manipulation section 113 is configured as a lateral recess, which has the shape of a circular arc. The circular arc points toward the central wall section 101, thereby indicating to the user the direction in which he must deform the resilient section to install the divider 100 in a filter basket. The protrusions 114 in this exemplary embodiment are exactly the same length as the thickness of the wall of the filter basket into which the divider is to be inserted. In the second lateral wall section, two protrusions 121 are formed. As is clear from FIG. 2, these two protrusions 121 are L-shaped. These L-shaped protrusions extend first in the lateral direction, approximately as far from the edge of divider 100 as the thickness of the wall of the filter basket into which the divider is to be inserted. The protrusions then extend in a direction perpendicular to the surface of the divider—in FIG. 1 toward the rear—approximately the same distance as the spacing between two holes in the wall of the filter basket into which the divider is to be inserted. The central wall section 101 has numerous openings or holes, which are arranged in rows and columns and thus form a grid-like structure. In this exemplary embodiment, the holes are oval in shape; however, the invention is not limited thereto. The central wall section 101 additionally has a bearing protrusion 103, which is positioned bearing against the bottom of the filter basket when the divider 100 is inserted into a filter basket. Said bearing protrusion 103 facilitates the vertical alignment of the divider relative to the filter basket during insertion. The wall sections 101, 110, and 120 merge into one another and are not necessarily sharply demarcated.

In this example, the slit-shaped notch 111 is rounded at its root to prevent the divider from becoming notched further in this region as a result of a large number of elastic deformations of the resilient section 112. In other words, the rounding serves to reduce stress peaks in the divider 100 when the resilient section 112 is in the deformed state.

FIGS. 3A to 4B show how this divider 100 can be inserted into a filter basket 10. First, the divider 100 is inserted into the filter basket 10 and the L-shaped protrusions 121 are inserted into two holes or openings 12, arranged one above the other, in the perforation of the filter basket. The divider 100 is then rotated about the L-shaped protrusions 121. At that time, with the aid of the manipulation section 113, the resilient section 112 is deformed toward the central wall portion 101 to temporarily decrease the lateral extension of the divider so that the protrusions 114 will not engage into the holes of the filter basket until the divider 100 has reached the desired position. The unattached ends of the L-shaped protrusions 121 engage around one of the crosspieces that are formed between adjacent openings of the perforation 12 of the filter basket. When the divider 100 has reached the desired position, which usually is precisely perpendicular to the two walls of the filter basket 10, the resilient section 112 is released and returns to its original position or shape, with the protrusions 114 engaging into two openings 12 in the wall of the filter basket 10. While the divider 100 is being pivoted about the L-shaped protrusions 121, the bearing protrusion 103 slides along the bottom of the filter basket and thus serves to ensure the proper vertical alignment of the divider 100.

The holes 102 and the protrusions 114 and 121 may also be arranged such that a divider 100 can also be anchored on one side or even on both sides in a similar divider 100. This allows the dividers 100 to have various lengths and/or heights, thereby enabling a highly individualized partitioning of a filter basket.

Figure 5:
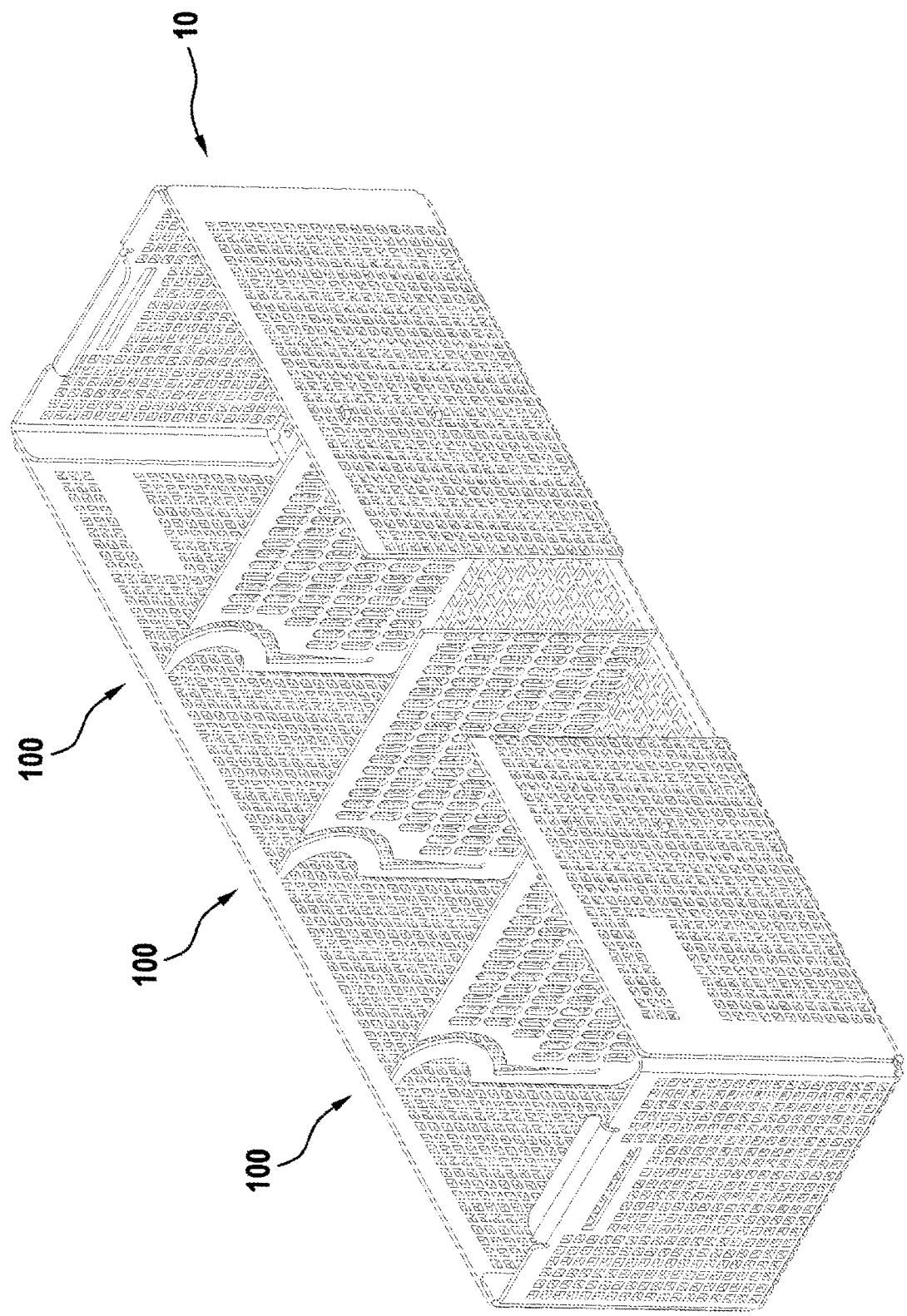
FIG. 5 shows a filter basket with multiple dividers according to FIG. 1.

FIG. 5 shows a filter basket 10, into which three dividers 100 of the first exemplary embodiment are inserted. In the view shown in FIG. 5, part of one side wall of the filter basket 10 has been cut away for purposes of illustration.

Figure 6:
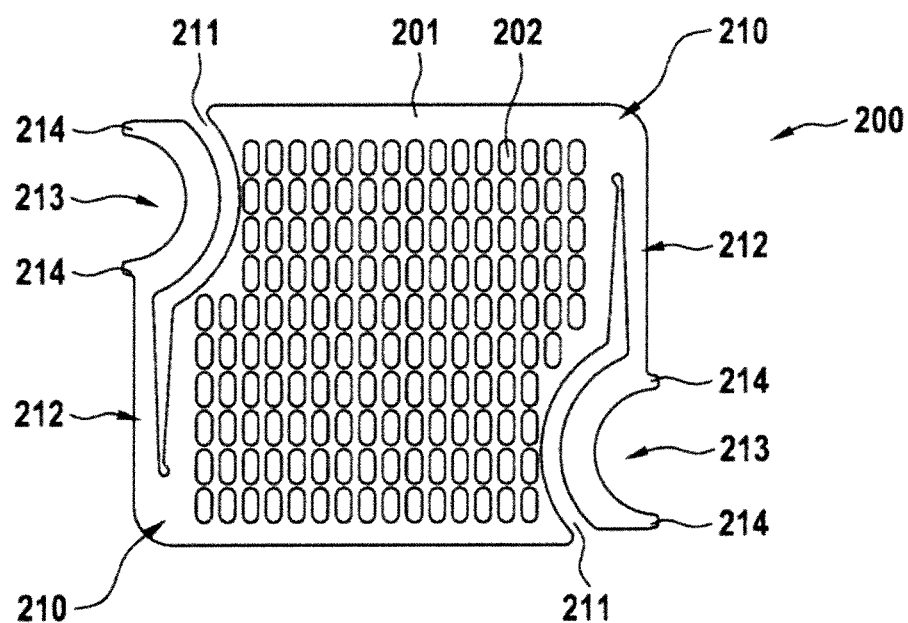
FIG. 6 shows a view of a second exemplary embodiment of the present invention.

A second exemplary embodiment of the present invention is shown in FIG. 6. A divider 200 has a central wall section 201 with holes 202 and two lateral wall sections 210. In each of these wall sections 210, a slit-shaped notch 211 is formed, which separates a resilient section 212 from the central wall section 201. On each resilient section 112, two protrusions 214 are formed, between which a manipulation section 213 is formed in each case, in the form of an arc-shaped or circular arc-shaped recess. While one of the two slit-shaped notches 211 extends into the divider 200 from the top, the other slit-shaped notch 211 extends into the divider 200 from the bottom. A rotationally symmetrical divider 200 is thereby formed, which no longer has an obvious top and/or bottom side. The divider 200 is also made of a metal.

Such a divider 200 is preferably inserted into a filter basket 10 such that first, those protrusions 114 on one of the two lateral wall sections 210 that are generally located closer to the bottom of the filter basket 10 are anchored in a wall of the filter basket 10. The divider 200 is then rotated or pivoted around these protrusions, and the insertion process continues as described for the first exemplary embodiment. However, it is also possible for those protrusions 114 on a wall section 210 that are generally located closer to the upper edge of the filter basket 10 to be anchored first in a wall of a filter basket 10.

The protrusions 114 of the two lateral wall sections 210 may also be arranged at the same height, however, making it irrelevant which protrusions are anchored first in which wall of the filter basket 10 or of another divider 100 or 200. It is also possible for both resilient sections 212 to be deformed, thus allowing all of the protrusions 114 to be anchored simultaneously in the respective wall of the filter basket 10 or in another divider 100, 200 by being inserted into the openings 12 thereof.

Figure 7:
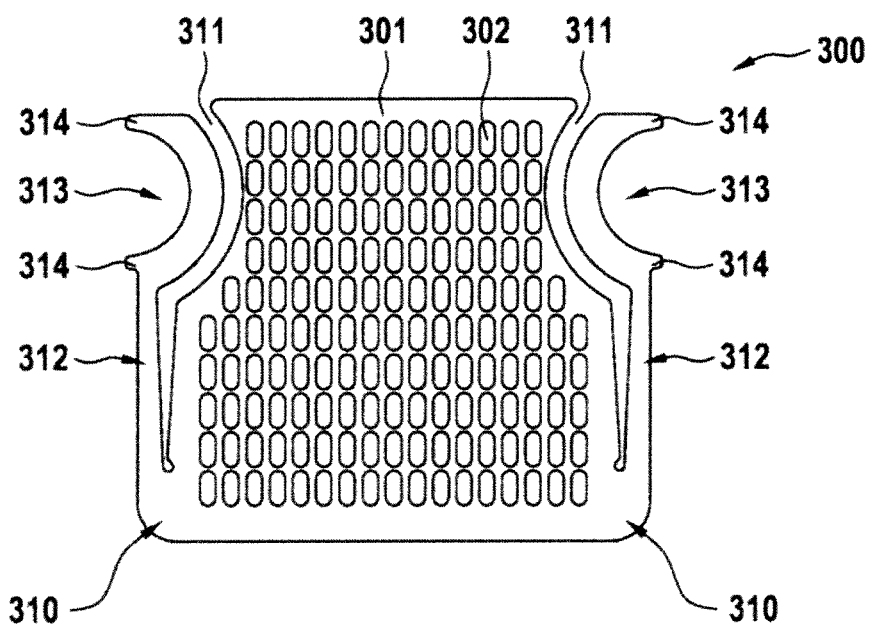
FIG. 7 shows a view of a third exemplary embodiment of the present invention.
Figure 8:
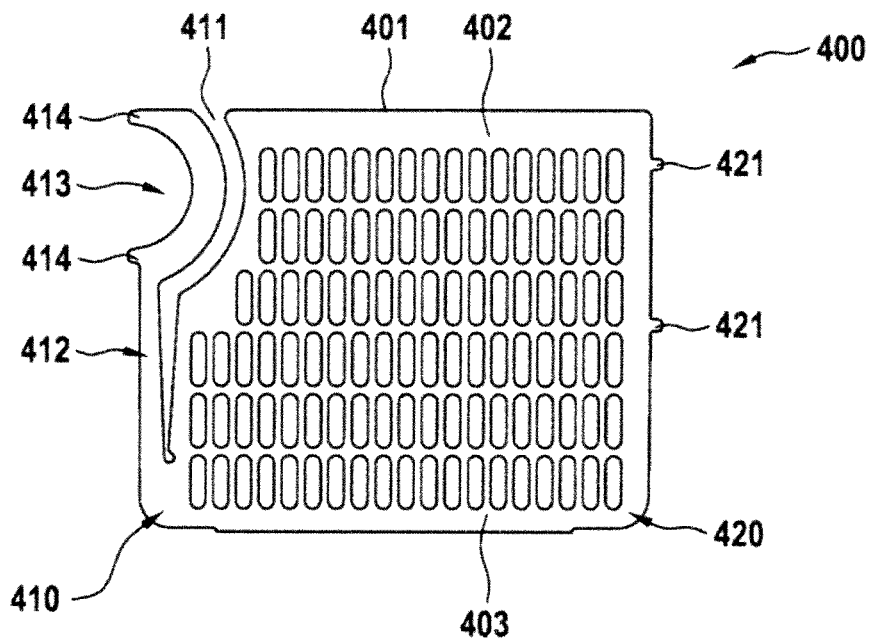
FIG. 8 shows a view of a fourth exemplary embodiment of the present invention.
Figure 9:
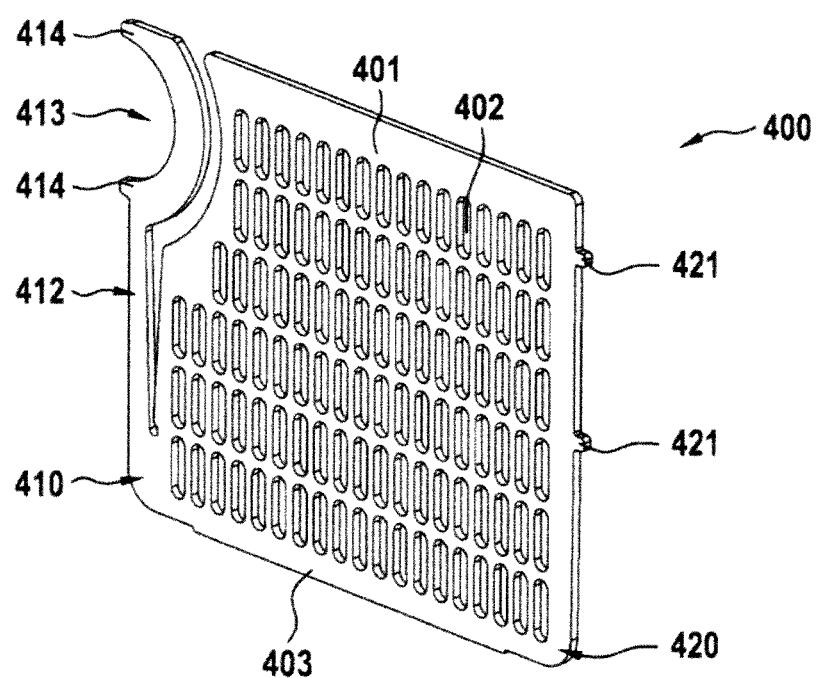
FIG. 9 shows a perspective view of the divider of FIG. 8.
Figure 10A:
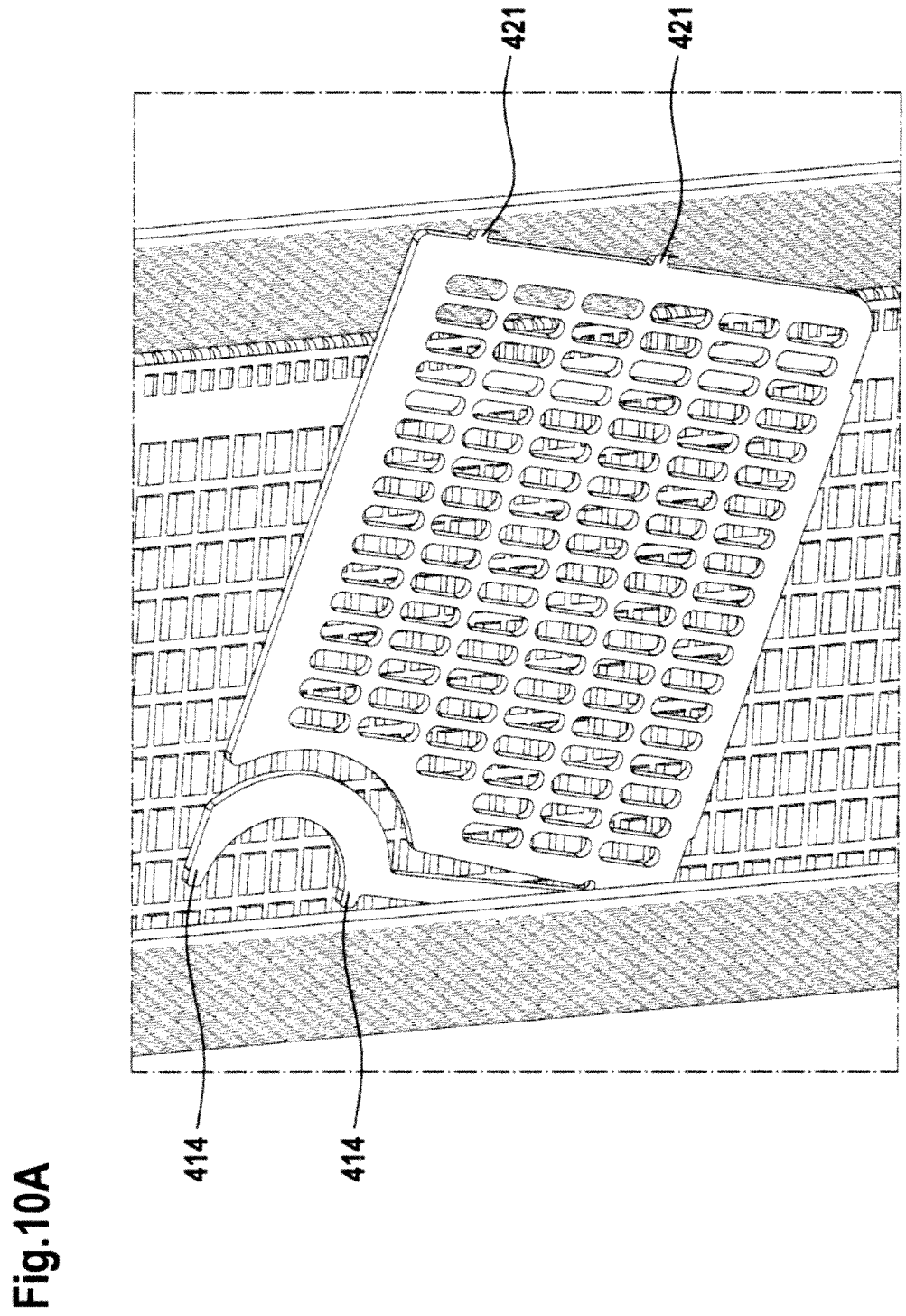
FIGS. 10A and 10B show the start of an installation of a divider of FIG. 8 into a filter basket.
Figure 10B:
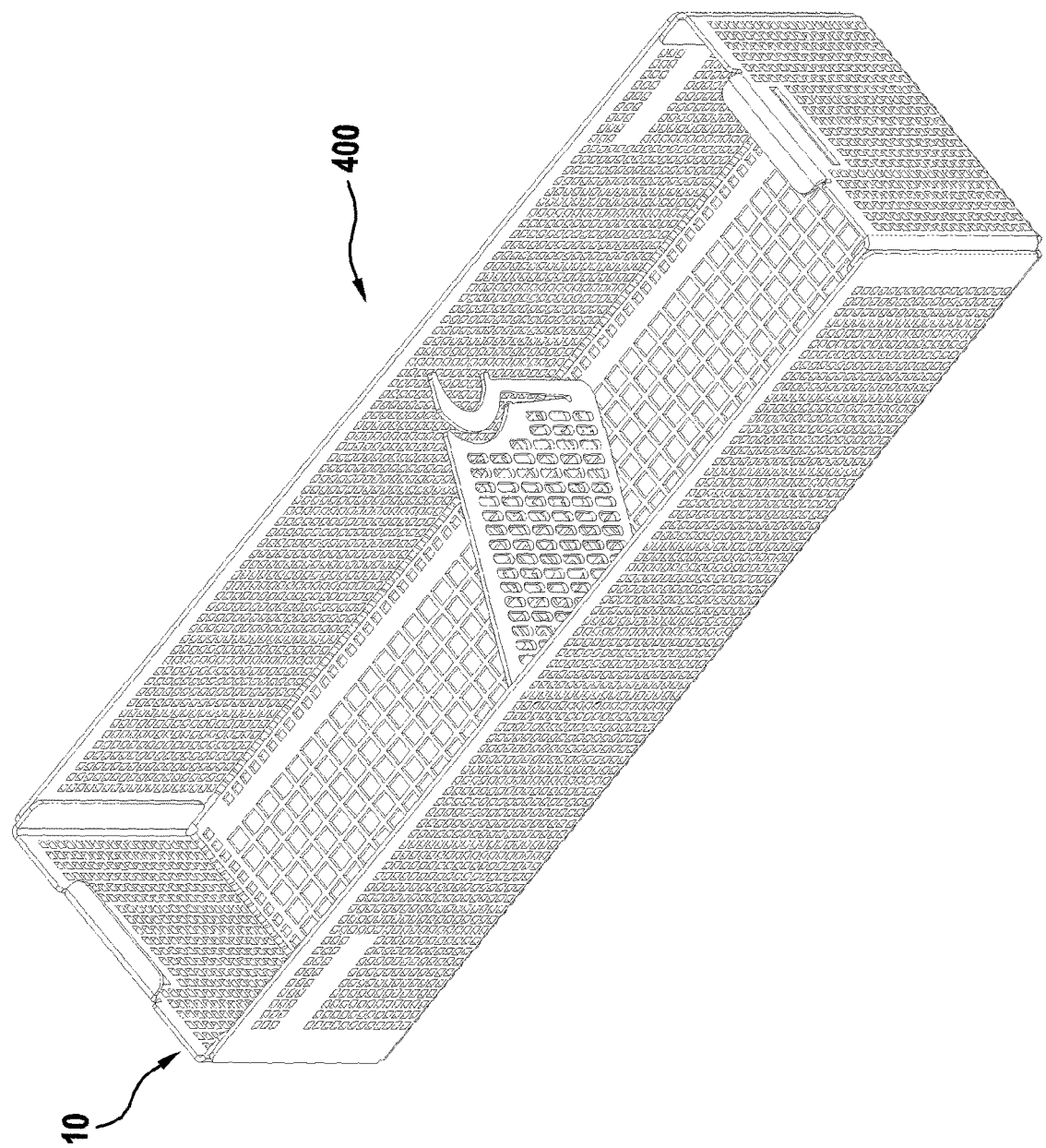
Figure 11A:
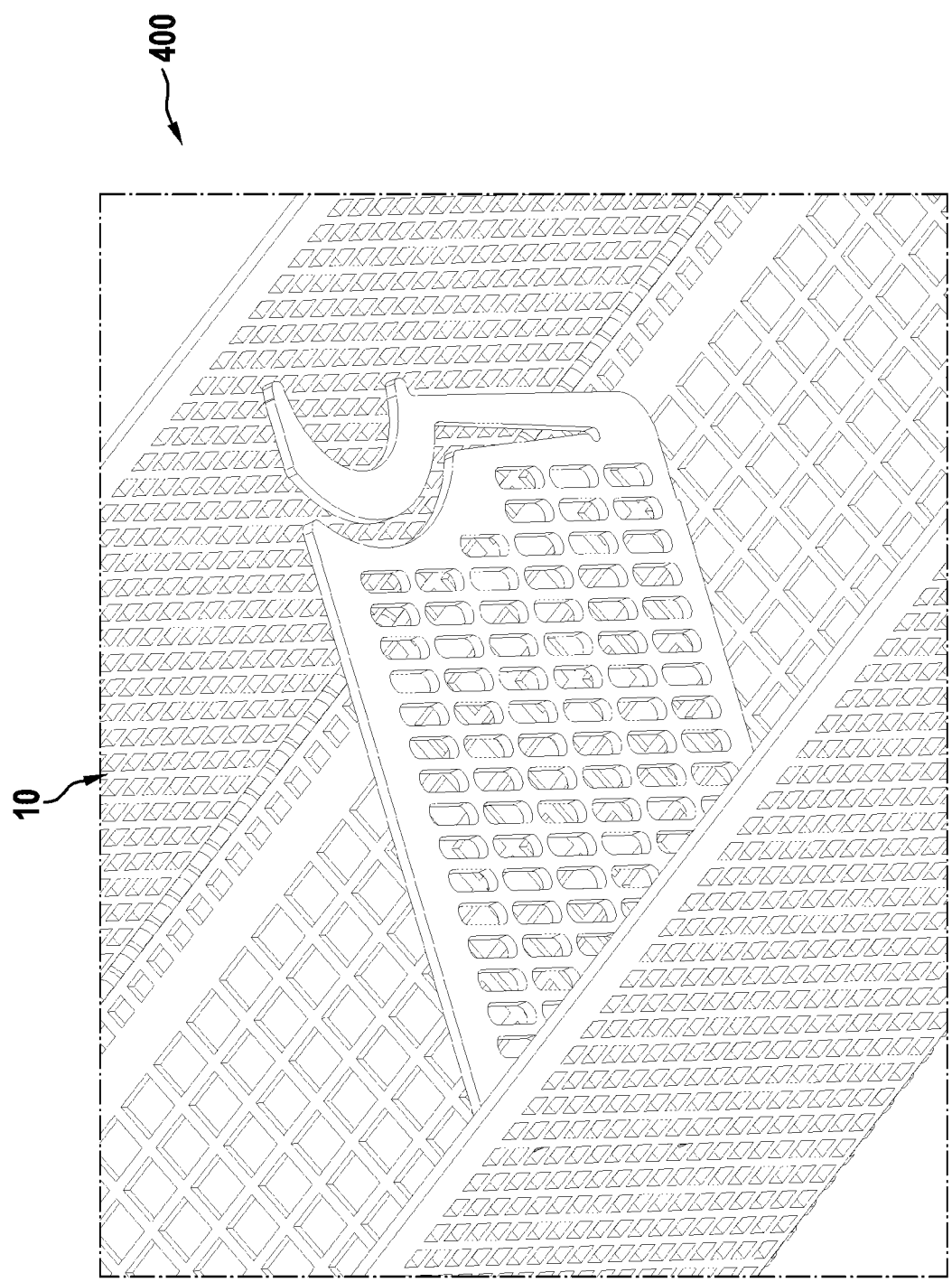
FIGS. 11A and 11B show the progression of an installation of a divider of FIG. 8 into a filter basket.
Figure 11B:
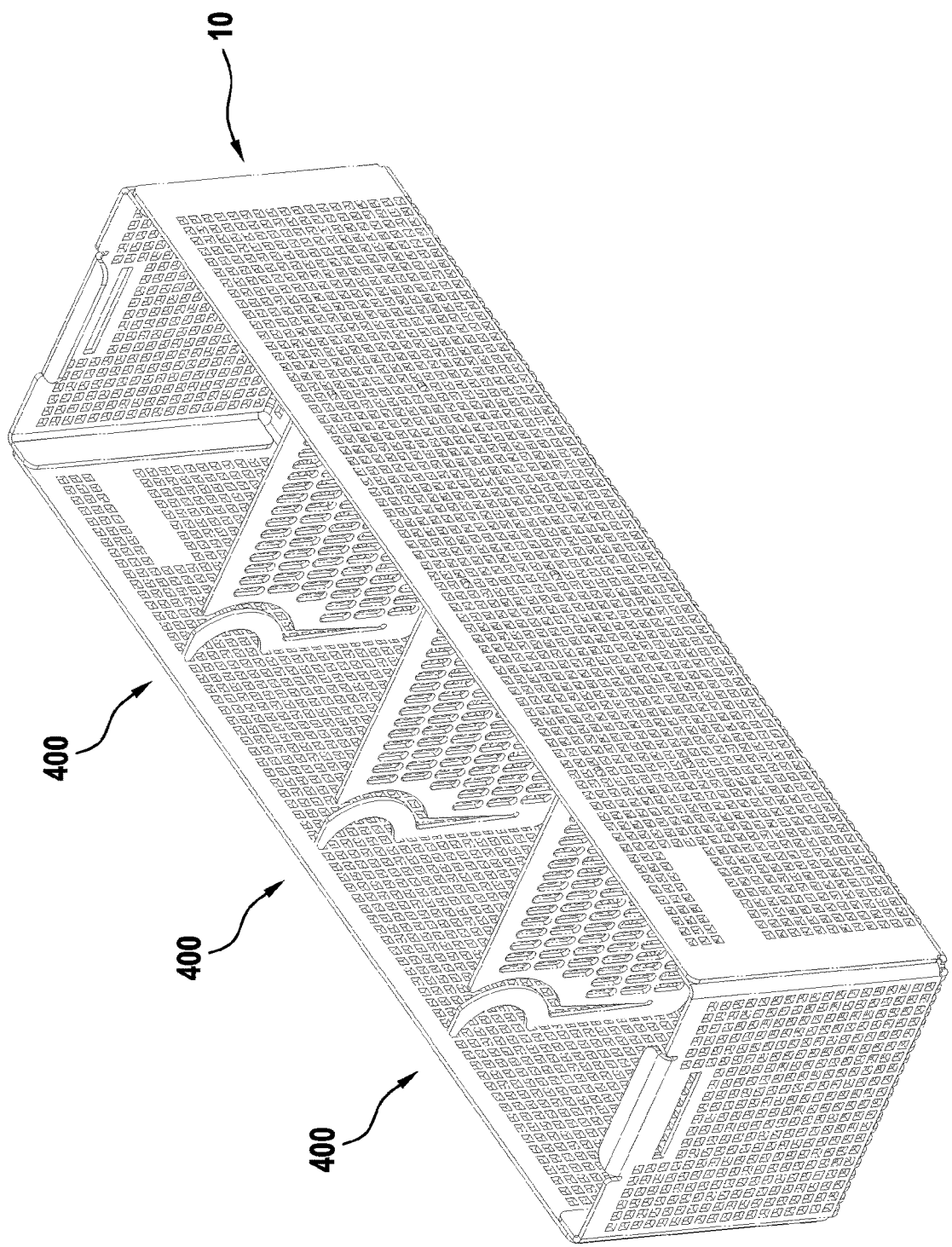
Figure 12:
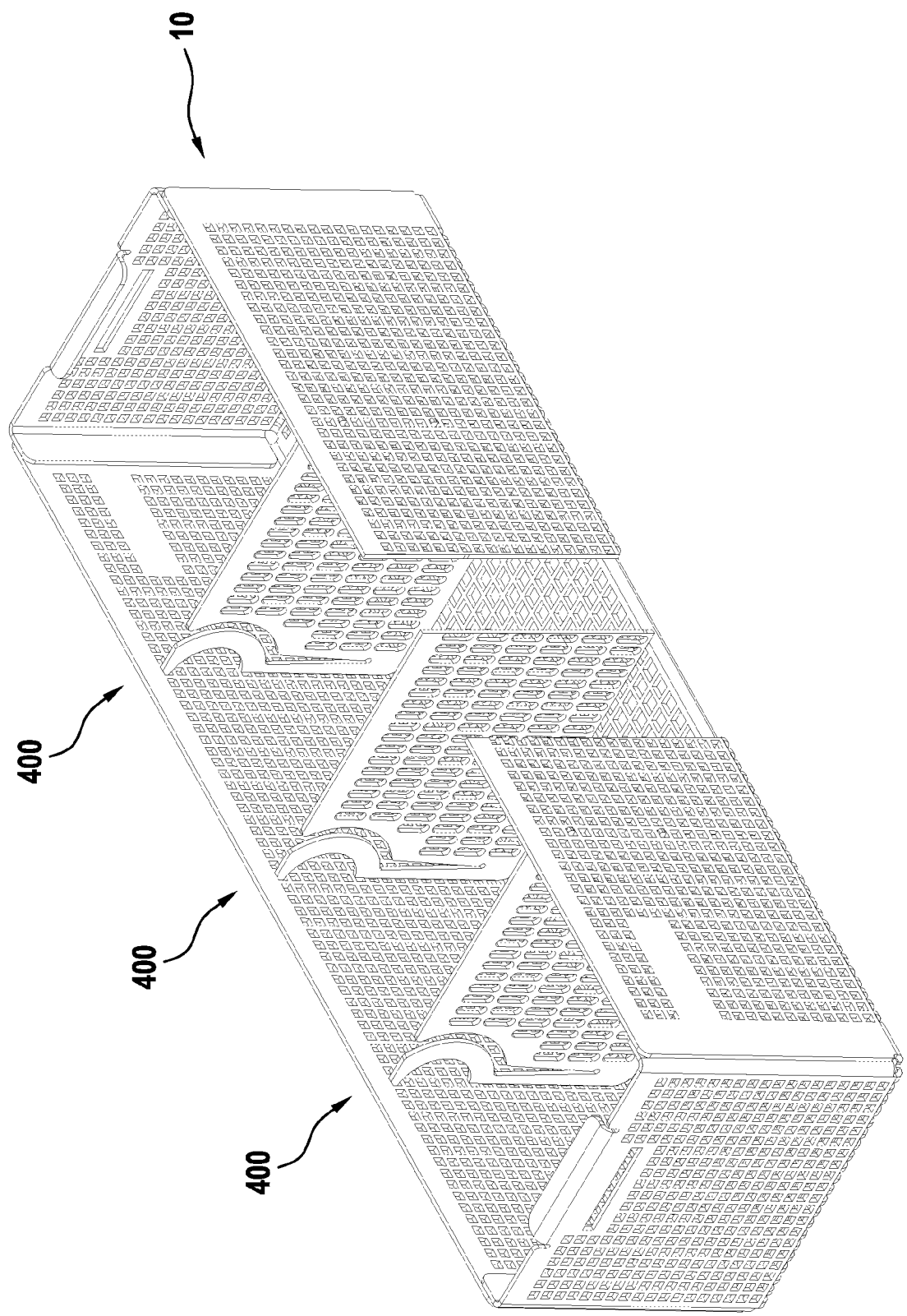
FIG. 12 shows a filter basket with multiple dividers according to FIG. 8.

In FIG. 7, a third exemplary embodiment of the present invention is shown. This divider 300 likewise has a central wall section 301 with holes 302 and two lateral wall sections 310. In each lateral wall section 310, a slit-shaped notch 311 is once again provided, which forms a resilient section 312, on which two protrusions 314 are again provided, between which a manipulation section 313 is formed in each case. In contrast to the second exemplary embodiment, the two slit-shaped notches 311 extend into the divider 300 from the same side, making the divider mirror-symmetrical. This divider 300 is inserted in essentially the same manner as is possible with the second exemplary embodiment. The third exemplary embodiment is made of a sturdy plastic.

In FIGS. 8 to 11, a fourth exemplary embodiment of the present invention is shown. The divider 400 of this fourth exemplary embodiment differs from the divider 100 of the first exemplary embodiment only in that the protrusions 421 are configured as lateral protrusions, whereas the protrusions 121 of the first exemplary embodiment are configured as L-shaped protrusions. The protrusions 421 of the fourth exemplary embodiment extend entirely within the plane of the dividing wall.

Numerous variations and modifications will emerge to a person skilled in the art from the various exemplary embodiments. The individual features of the exemplary embodiments can be meaningfully combined with one another in many ways. For example, a bearing protrusion 103 may also be formed on the lower side of the divider 300 or on the upper side and/or the lower side of the divider 200. The materials can likewise be interchanged as desired.

The slit-shaped notches 111, 211, 311 are not limited to a specific shape, and slit-shaped does not mean that the notch must be particularly narrow. The notch must enable sufficient elastic deformability of the resilient section 112, 212, 312, and at the same time should not be so large that the divider 100, 200, 300 can no longer effectively partition the filter basket 10. This is also dependent upon the size of the elements that are to be stored in the filter basket.

The invention claimed is:

1. A divider for a sterilization filter basket for the sterilization of medical instruments, the divider comprising a first lateral wall section, a second lateral wall section and a central wall section therebetween,
   the divider comprising a top side, a bottom side opposite the top side, and a vertical height extending between the top side and bottom side,
   the central wall section having a plurality of openings,
   the first lateral wall section equipped with a slit-shaped notch extending along a majority of the vertical height of the divider, so that a lateral region of the first lateral wall section, which is separated by the slit-shaped notch, is formed as a resilient section, wherein the resilient section has a number of protrusions extending at least in a lateral direction, and
   the second lateral wall section having a number of protrusions extending at least partially in the lateral direction.

2. The divider for a sterilization filter basket for the sterilization of medical instruments according to claim 1, wherein at least one protrusion of the second lateral wall section extends at least partially in a direction perpendicular to an extension plane of the central wall section.

3. The divider for a sterilization filter basket for the sterilization of medical instruments according to claim 2, wherein the at least one protrusion of the second lateral wall section is substantially L-shaped in configuration and extends from the second lateral wall section first in the lateral direction, and in subsequent extension in a direction perpendicular to a surface of the central wall section.

4. A divider for a sterilization filter basket for the sterilization of medical instruments, the divider comprising two lateral wall sections and a central wall section therebetween,
   the divider comprising a top side, a bottom side opposite the top side, and a vertical height extending between the top side and bottom side,
   the central wall section having a plurality of openings, and
   each of the lateral wall sections having a slit-shaped notch extending along a majority of the vertical height of the divider, so that a lateral region of each lateral wall section, which is separated by the slit-shaped notch, is formed as a resilient section, wherein each resilient section has a number of protrusions extending at least in a lateral direction.

5. The divider for a sterilization filter basket for the sterilization of medical instruments according to claim 4, wherein the divider is mirror-symmetrical.

6. The divider for a sterilization filter basket for the sterilization of medical instruments according to claim 4, wherein the divider is rotationally symmetrical.

7. The divider for a sterilization filter basket for the sterilization of medical instruments according to claim 4, wherein each lateral wall section has at least two protrusions.

8. The divider for a sterilization filter basket for the sterilization of medical instruments according to claim 4, wherein on one resilient section a manipulation section is formed.

9. The divider for a sterilization filter basket for the sterilization of medical instruments according to claim 8, wherein the manipulation section is formed between two protrusions.

10. The divider for a sterilization filter basket for the sterilization of medical instruments according to claim 8, wherein the manipulation section is configured as a lateral recess.

11. The divider for a sterilization filter basket for the sterilization of medical instruments according to claim 4, wherein the divider is made of metal.

12. The divider for a sterilization filter basket for the sterilization of medical instruments according to claim 1, wherein the first lateral wall section, second lateral wall section and central wall section conform to and lie entirely within a single plane.

13. The divider for a sterilization filter basket for the sterilization of medical instruments according to claim 12, wherein the protrusions conform to and lie at least partially within the single plane.

14. The divider for a sterilization filter basket for the sterilization of medical instruments according to claim 12, wherein the slit-shaped notch provides space for the resilient section to flex toward the central wall portion entirely within the single plane.

15. The divider for a sterilization filter basket for the sterilization of medical instruments according to claim 1, wherein the number of protrusions of the resilient section comprises a first protrusion spaced a first distance from the top side and a second protrusion spaced a second distance from the top side, the second distance greater than the first distance.

16. The divider for a sterilization filter basket for the sterilization of medical instruments according to claim 15, further comprising a manipulation recess between the first protrusion and the second protrusion.

17. The divider for a sterilization filter basket for the sterilization of medical instruments according to claim 1, wherein the slit-shaped notch comprises a first section having an open end on the top side of the divider and extending away from the open end in a direction toward the second lateral wall section.

18. The divider for a sterilization filter basket for the sterilization of medical instruments according to claim 1, wherein the first lateral wall section comprises a convex wall bordering a first side of the slit-shaped notch and a concave wall bordering a second side of the slit-shaped notch opposite the first side.

19. The divider for a sterilization filter basket for the sterilization of medical instruments according to claim 1, wherein each lateral wall section has at least two protrusions.

20. A divider for a sterilization filter basket for the sterilization of medical instruments, the divider comprising a first lateral wall section, a second lateral wall section and a central wall section therebetween, the first lateral wall section having a slit-shaped notch therein, so that a lateral region of the first lateral wall section, which is separated by the slit-shaped notch, is formed as a resilient section, the resilient section having a first protrusion extending at least partially in a lateral direction, the second lateral wall section having a second protrusion extending at least partially in the lateral direction, the second protrusion forming a pivot element configured to pivotably connect the divider to a first support, the resilient section and first protrusion forming a releasable engagement element configured to releasably engage a second support, wherein, when the second protrusion is pivotably connected to the first support, the divider is pivotable relative to the first support to a desired position between the first and second supports, and the first protrusion is releasably engageable with the second support in a biased state to secure the divider in the desired position between the first and second supports.

* * * * *